(12) United States Patent
Brunner

(10) Patent No.: US 7,337,896 B2
(45) Date of Patent: Mar. 4, 2008

(54) PACKAGE FOR DENTAL PRODUCT, WITH A LABEL ASSIGNED TO THE PRODUCT

(75) Inventor: Gideon Brunner, Basel (CH)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 11/401,211

(22) Filed: Apr. 10, 2006

(65) Prior Publication Data
US 2006/0260958 A1    Nov. 23, 2006

(30) Foreign Application Priority Data
Apr. 12, 2005   (EP)   .................. 05007914

(51) Int. Cl.
*B65D 83/10* (2006.01)
(52) U.S. Cl. ................. 206/63.5; 206/368; 206/469
(58) Field of Classification Search .......... 206/63.5, 206/368, 369, 469, 484, 532, 534, 564, 813; 433/2, 3
See application file for complete search history.

(56) References Cited

U.S. PATENT DOCUMENTS

| | | | |
|---|---|---|---|
| 3,924,748 A * | 12/1975 | Braverman | .............. 206/534.1 |
| 4,526,404 A | 7/1985 | Vazquez et al. | |
| 5,350,059 A * | 9/1994 | Chester et al. | .............. 206/63.5 |
| 5,762,192 A * | 6/1998 | Jacobs et al. | ............... 206/369 |
| 5,887,707 A | 3/1999 | Anascavage et al. | |
| 6,382,420 B1 * | 5/2002 | Bouthiette | .................. 206/534 |

FOREIGN PATENT DOCUMENTS

| | | |
|---|---|---|
| WO | WO 92/08419 | 5/1992 |
| WO | WO 93/02631 | 2/1993 |
| WO | WO 2004/002357 | 1/2004 |

OTHER PUBLICATIONS

European Search Report from priority application EP 05 007 914.1.

* cited by examiner

*Primary Examiner*—Luan K Bui
(74) *Attorney, Agent, or Firm*—Rissman Jobse Hendricks & Oliverio LLP

(57) ABSTRACT

A package for a dental product, in particular for a prosthetic structure, has several product-receiving recesses which are formed in a product holder from the direction of the top face thereof. The product-receiving recesses are each spanned by a pull-off strip which is defined by a weakening and can be detached from a remaining area of a self-adhesive film affixed to the top face of the product holder. Applied to each pull-off strip there is a reference which identifies a product held in the product-receiving recess spanned by the pull-off strip.

9 Claims, 2 Drawing Sheets

PACKAGE FOR DENTAL PRODUCT, WITH A LABEL ASSIGNED TO THE PRODUCT

FIELD OF THE INVENTION

The present invention relates to a package for a dental product.

BACKGROUND

One known package for a dental product, namely an implant, is disclosed in WO 2004/002357. This package has a lower part made of metal foil and with a product-receiving recess, and an upper part, likewise made of metal foil, that closes the product-receiving recess. The two parts are welded to one another. The product-receiving recess is closed by the upper part such that the product-receiving recess is substantially free from air, water and moisture. To open the package, the upper part has a pull-off strip.

Dental products, such as prosthetic superstructures, are often custom-made products. These custom-made products are generally provided with a specific reference, which may be applied on the package for example. After removal of the product from the package, the package is normally disposed of.

SUMMARY OF THE INVENTION

The present invention relates to a package which easily allows a link between a reference provided for a custom-made product to be maintained even after the product has been removed from the package and even when the package is disposed of.

According to one embodiment of the invention, the package has a product holder comprising an upwardly open product-receiving recess. A film is arranged on the product holder to span the product-receiving recess, the film having a pull-off strip to permit removal of the product. The film has a weakening that delimits the pull-off strip, and the pull-off strip can be completely removed. The pull-off strip also bears an individual reference assigned to the product, and the strip is made self-adhesive on a side directed toward the product-receiving recess.

In one embodiment, the self-adhesive side of the pull-off strip is covered by a detachable protective film. The film may be self-adhesive across its entire surface on the side directed toward the product holder, and this strip is with that self-adhesive surface affixed to the product holder. The film may comprise a transparent plastic.

In addition, the product holder may have several product-receiving recesses that are each spanned by the film, with the film having one pull-off strip per product receiving recess to permit individual product removal.

An upwardly open groove may be provided in the product holder which extends from the product-receiving recess to a lateral edge of the product holder, and which is spanned by the pull-off strip.

The product holder may also have an auxiliary product receiving recess which is spanned by the film, the film having an opening tab to permit removal of an auxiliary product from the auxiliary product-receiving recess. The opening tab may be defined by a further weakening of the film. The product holder may have several such auxiliary product-receiving recesses, and the film have one opening tab per recess to permit individual opening of each auxiliary product-receiving recess.

A lateral and upwardly open auxiliary recess may be provided between the auxiliary product-receiving recess and a side face of the product holder.

The product holder may be arranged in a shell of a box with a removable lid.

In one embodiment, a film, preferably a self-adhesive film, is applied on the top face of the product holder. This film spans the product-receiving recess and has a pull-off strip which is separated from a remaining area of the film by means of a linear weakening, preferably a perforation. The line of weakening extends such that it is possible to detach the pull-off strip from the remaining area of the film by pulling. The pull-off strip is provided with a reference, for example a printed reference, clearly assigned to a product received in the product-receiving recess under the pull-off strip.

Since the pull-off strip is made self-adhesive on its side directed toward the product-receiving recess, it is possible for a dentist, for example, to remove a product from the package and stick the pull-off strip bearing the product reference onto a records form, a patient file or the like, for example, as a result of which the connection between reference and product is very easily maintained.

The self-adhesive side of the pull-off strip is preferably covered by a protective film such that the product received in the product-receiving recess cannot adhere to the pull-off strip. After the pull-off strip has been separated from the package, the protective film can be removed and then affixed for example to the records form or the like.

In another advantageous embodiment, the package has several product-receiving recesses, each one closed by a pull-off strip.

In another advantageous embodiment, the package has one or more auxiliary product-receiving recesses, for example for screws. The auxiliary product-receiving recesses are likewise spanned by the film which in the case of the auxiliary product-receiving recesses has opening tabs which are defined by further linear weakenings of the film and which cannot be completely detached from the film.

Further particular advantages and functions of the package will become clear from the following detailed description and drawings of a preferred embodiment.

BRIEF DESCRIPTION OF THE FIGURES

The invention is explained in more detail below on the basis of an illustrative embodiment depicted in the drawings, in which, purely diagrammatically.

DETAILED DESCRIPTION

Figure 1:
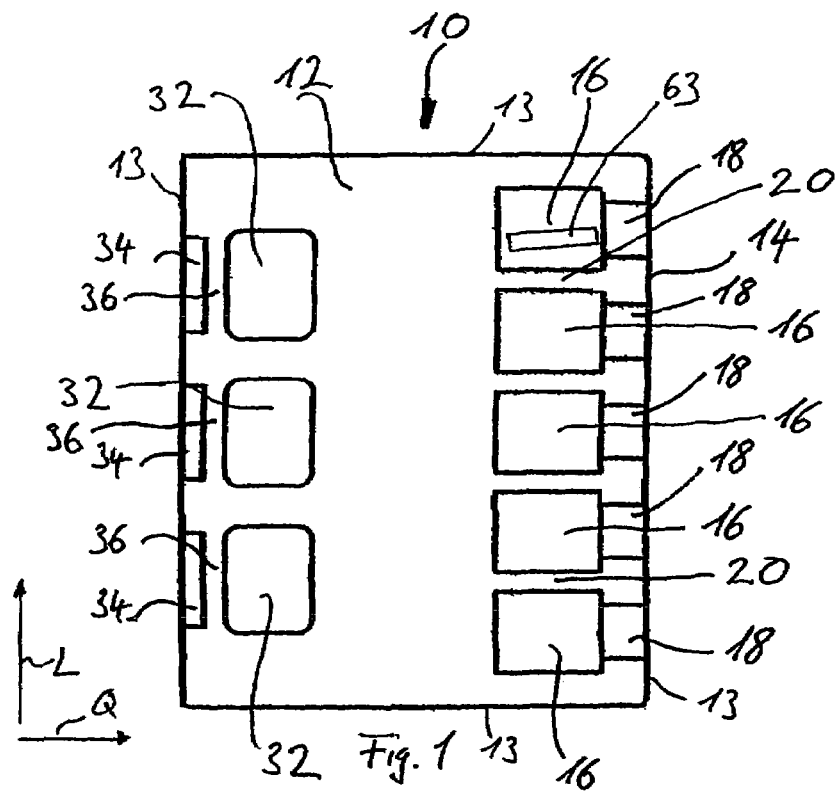
FIG. 1 shows a plan view of a product holder with five product-receiving recesses and three auxiliary product-receiving recesses.
Figure 2:
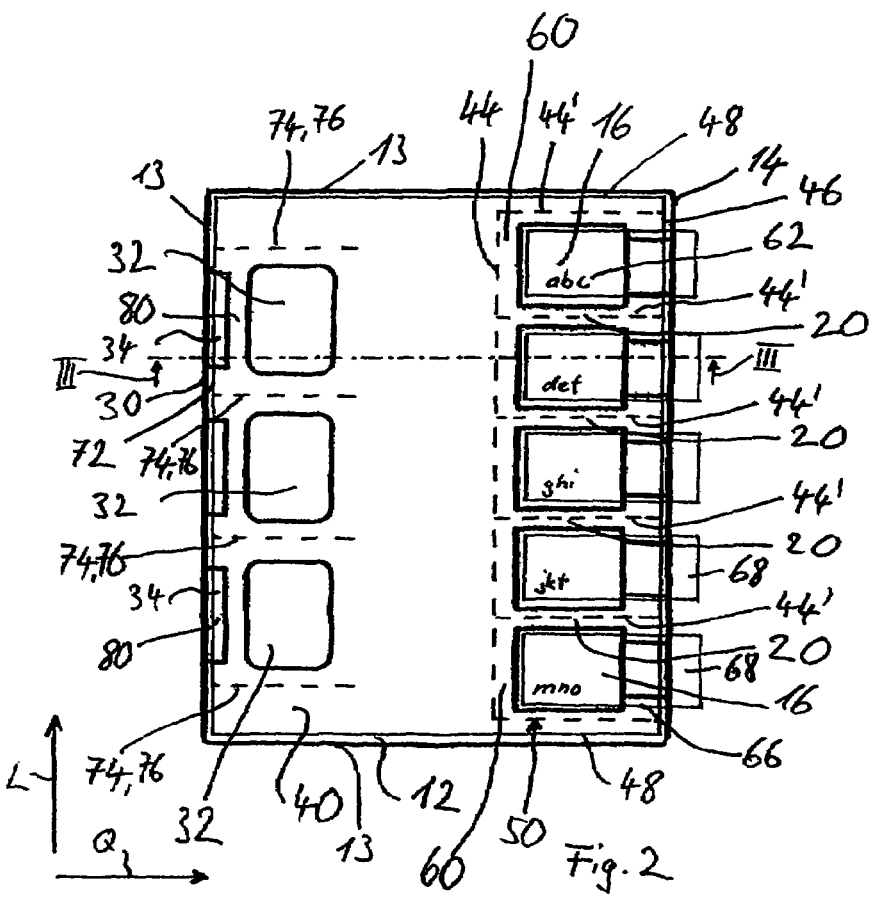
FIG. 2 shows a plan view of the product holder according to FIG. 1 with a film affixed to it, with pull-off strips which are defined by perforations and which close the product-receiving recesses, and with opening tabs which are defined by perforations and which close the auxiliary product-receiving recesses.
Figure 3:
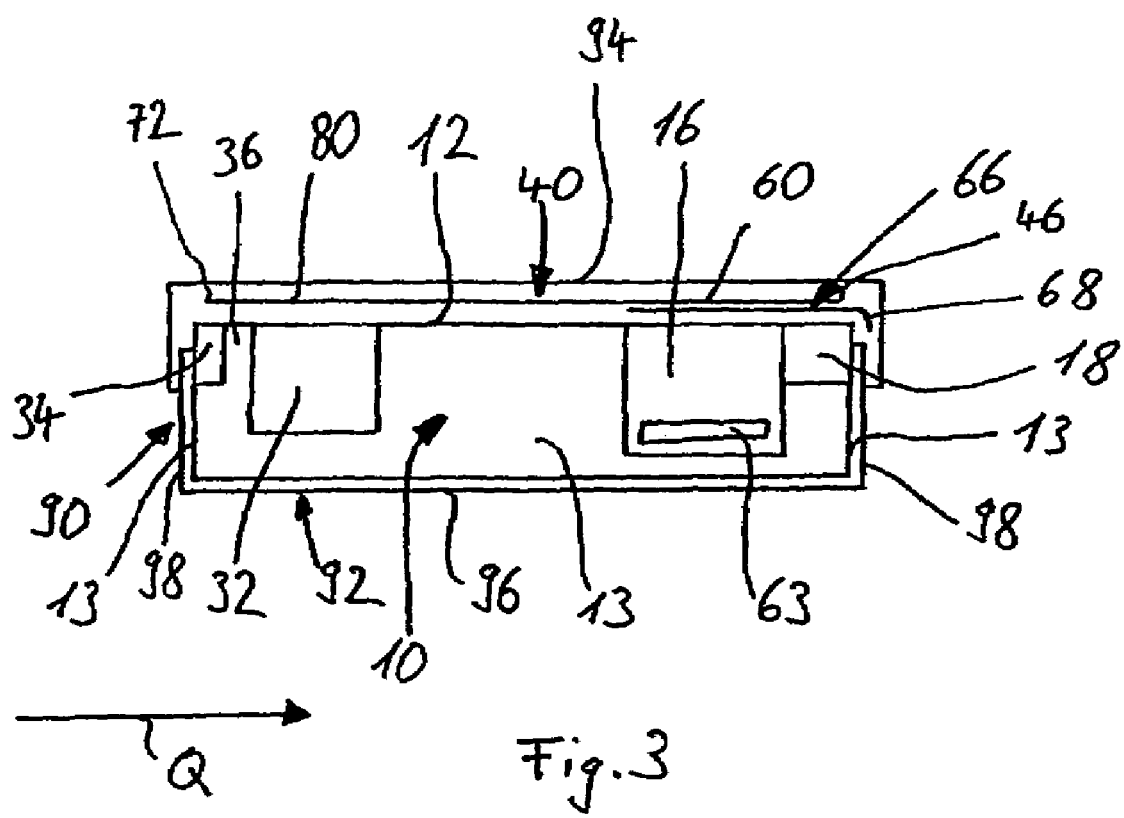
FIG. 3 shows a cross-sectional view of the product holder inserted into a box composed of a shell and a lid, taken along the section line III indicated in FIG. 2.

A product holder 10 according to the embodiment shown in FIG. 1 to FIG. 3 has a rectangular top face 12 defining a longitudinal direction L and a transverse direction Q, the corners of this rectangle being rounded. At the edge of the top face 12, and protruding downward from the latter, the product holder 10 has four side walls 13 (see FIG. 3). The side walls 13 all have the same height.

Five product-receiving recesses 16 are formed along one long side 14 of the two long sides 14 and 30 of the top face 12. They are at a distance of 5 mm, for example, from the associated side wall 13. One of these product-receiving recesses 16 is described below.

The product-receiving recess 16 is a square recess formed in the product holder 10 from the direction of the top face 12. Edges of the product-receiving recess 16 extend in the longitudinal direction L, transverse direction Q, and in a direction at right angles to the longitudinal direction L and the transverse direction Q, the edges and corners of the product-receiving recess 16 being rounded. Measured from the direction of the top face 12, the depth of the product-receiving recess 16 is slightly less than the height of the side walls 13.

Each product-receiving recess 16 is assigned a groove 18 that is open toward the top. Each of the grooves 18 is formed in the product holder 10 from the direction of the top face 12 and forms a connection between the product-receiving recess 16 and the side wall 13 bordering the long side 14. Measured from the direction of the top face 12, the groove 18 is approximately one third as deep as the product-receiving recess 16. The groove 18 is narrower in the longitudinal direction L than the product-receiving recess 16 and is arranged centrally with respect to the latter.

A transverse web 20 lies in each case between two product-receiving recesses 16.

Three auxiliary product-receiving recesses 32 are formed along the other long side 30 of the two long sides 14 and 30 of the top face 12. One of these auxiliary product-receiving recesses 32 is described below.

The auxiliary product-receiving recess 32 is a square recess formed in the product holder 10 from the direction of the top face 12. The edges of the auxiliary product-receiving recess 32 extend in the longitudinal direction L, transverse direction Q, and in a direction at right angles to the longitudinal direction L and the transverse direction Q, the edges and corners of the further auxiliary product-receiving recess 32 being rounded. A depth of the product-receiving recess 32 is slightly less than the height of the side walls 13.

From the top face 12 and from the side face 13 bordering the long side 30, a square auxiliary recess 34 is formed in the product holder 10 for each product-receiving recess 32. The auxiliary recesses 34 are each separated from the auxiliary product-receiving recess 32 by a longitudinal web 36.

A transparent plastic film 40, completely self-adhesive on one side, is affixed to the top face 12 of the product holder 10. The one-piece film 40 spans the product-receiving recesses 16 and the auxiliary product-receiving recesses 32 and extends at least almost to the edge of the top face 12.

The film 40 has a straight, linear perforated section 44 which extends in the longitudinal direction L and which is arranged in such a way that the product-receiving recesses 16 lie between the perforated section 44 and the long side 14. Further transversely extending perforated sections 44' connect the perforated section 44 extending in the longitudinal direction to an edge 46 of the film 40 contiguous to the long side 14 of the product holder 10 and extending in the longitudinal direction L, such that they extend at least almost centrally on the transverse web 20 lying between two product-receiving recesses 16 or between a transversely extending contiguous edge 48 of the film 40 and the respective outermost product-receiving recess 16 in the longitudinal direction L.

The perforated section 44 extending in the longitudinal direction L, together with the transversely extending perforated sections 44', form a linear weakening 50, such that the film 40 has for each product-receiving recess 16 a pull-off strip 60 that spans the product-receiving recess 16. Each pull-off strip 60 is completely delimited by the linear weakening 50 and a part of that edge 46 of the film 40 extending in the longitudinal direction L.

Each pull-off strip 60 is provided with a reference 62 clearly identifying the product 63, here a prosthetic superstructure, received in the product-receiving recess 16. In the drawing, the reference is shown by way of example as sequences of letters "abc", "def", "ghi", "jkl" and "mno", although of course the references 62 can be formed by any desired number of individual characters and preferably using letters, numbers, punctuation marks, etc., in any desired alphabets or writing systems as individual characters. Instead of the sequence of letters, a barcode can also be used as reference.

Since the film 40 is self-adhesive across its entire surface, and therefore the side of the pull-off strips 60 directed toward the product-receiving recesses 16 is also self-adhesive, the exposed area of each pull-off strip 60, e.g., at least the area covering the product-receiving recess 16, and optionally also the area covering the groove 18, is preferably completely covered by a protective film 66 in order to ensure that the products 63 held in the product-receiving recess 16 do not stick to it. To make it easier to grip and remove the pull-off strip 60 for removal of the product 63 located in the product-receiving recess 16, the protective film 66 has a tab 68 protruding past that edge 46 of the film 40 extending in the longitudinal direction L. This also facilitates the subsequent peeling-off of the protective film 66 from the separated pull-off strip 60.

From a further edge 72 of the film 40 located close to the other long side 30 of the product holder 10 and extending in the longitudinal direction L, perforated sections 74 extend in the direction of the transverse edges of the film 40. Corresponding to the transversely extending perforated sections 44', the perforated sections 74 extend centrally between the auxiliary product-receiving recesses 32 or centrally between the outermost auxiliary product-receiving recess 32 in the longitudinal direction L and the transversely extending, contiguous edge of the film 40. The length of the perforated sections 74 is chosen such that, viewed from the other long edge 72, these end a short distance behind the auxiliary product-receiving recesses 32.

The perforated sections 74 form a linear weakening 76 through which opening tabs 80 are defined. Each opening tab 80 completely spans one of the auxiliary product-receiving recesses 32 and at least partially spans an auxiliary recess 34 assigned to this auxiliary product-receiving recess 32.

The opening tabs 80 preferably bear a description for identifying the auxiliary products held in the auxiliary product-receiving recess 32 lying underneath, for example a screw for securing the prosthetic superstructure to an implant. Analogously to the protective film 66 of the pull-off strip 60, a further protective film can cover the exposed area of each opening tab 80 spanning the auxiliary product-receiving recess 32.

The product holder 10 is fitted in a conventional box 90 (see FIG. 3) composed of a shell 92 and of a lid 94 in a generally known manner. The shell 92 has a rectangular base surface 96 and four side walls 98. The dimensions of this shell 92 are chosen such that the product holder 10 can be inserted into the shell 92 and the side walls 13 of the product holder 10 bear on the side walls 98 of the shell 92. The depth of the shell 92 is chosen such that, with the product holder 10 inserted, the top face 12 of the product holder 10 comes to lie slightly above the edge of the shell 92. The lid 94 can be fitted onto the shell 92 in a known manner.

A preferred material for the product holder 10 is a high impact polystyrene SB/HK, with a bright coloration. The product holder is produced, for example, by thermosetting of a plastic web or by injection molding.

The box 90 is preferably produced using a polymethyl-methacrylate-based polymer, for example the product bearing the trade name Oroglas 327. The lid of the box 90 is preferably transparent.

The package according to one embodiment of the invention is used as follows. The product holder 10 is inserted into the shell 92 of the box 90. A product 63, for example a prosthetic structure, is then fitted in the product-receiving recess 16. An auxiliary product, for example one or more screws of the same type, is then fitted into the further product-receiving recess 32. The above-described product holder 10 is suitable for receiving separately a maximum of five individual products and a maximum of three auxiliary products of different type.

In a following step, the film 40 is affixed. The marking of the film 40 with various details concerning the product and manufacturer, and in particular the marking of the pull-off strips 60, is preferably done before the film 40 is affixed. The protective films 66 are applied to the film 40 before the latter is affixed to the top face 12 of the product holder 10.

In a further step, the lid 94 is fitted onto the box 90 and, for example, prepared for dispatch to a customer of the manufacturer and dispatched.

The customer, for example a dentist, removes the lid 94 from the box 90 before use. After removal of the lid 94, the products 63 and the auxiliary products are still held securely in the product holder 10 by the film 40. The groove 18 makes it easier to grip the tab 68 of the protective film 66 and of each associated pull-off strip 60. The weakening 50 allows each pull-off strip 60 to be detached completely from the film 40 without difficulty, without any danger of another product-receiving recess 16 being inadvertently opened too.

After detachment of the pull-off strip 60, the protective film 66 is removed from the pull-off strip 60, as a result of which the self-adhesive surface of the pull-off strip 60 is exposed. The pull-off strip 60 is then attached to a records form, a patient file or the like. By means of the reference 62 being on the pull-off strip 60, it is very easy to transfer the reference 62 from the package of the product 63 to the records sheet or the like, without introducing an additional source of error.

If necessary, the auxiliary product can be removed from the auxiliary product-receiving recess 32. The auxiliary recess 34 makes it easier to grip the opening tab 80. In contrast to the pull-off strip 60, the opening tab 80 is not separated from the film 40 and, after removal of the auxiliary product, can be closed again by virtue of the self-adhesive surface. When the opening tab 80 is lifted for the first time, a connection between film 40 and opening tab 80 is separated along the line of weakening 76.

Other modifications and variations will readily suggest themselves to a person of ordinary skill in the art. The invention is intended to encompass all such modifications and variations that fall within the scope of the appended claims.

The invention claimed is:

1. A package for a dental product, which package has a product holder comprising an upwardly open product-receiving recess, and a film arranged on the product holder and which spans the product-receiving recess and has a pull-off strip to permit removal of the product, wherein the film has a weakening that delimits the pull-off strip, and said pull-off strip can be completely removed, the pull-off strip also bearing an individual reference assigned to the product and being made self-adhesive on a side directed toward the product-receiving recess, and wherein said self-adhesive side of the pull-off strip is covered by a detachable protective film which protrudes past the pull-off strip thereby forming a tab.

2. The package of claim 1, wherein the film is self-adhesive across its entire surface on the side directed toward the product holder and wherein the self-adhesive surface is affixed to the product holder.

3. The package of claim 1, wherein the film comprises transparent plastic.

4. The package of claim 1, wherein the product holder has several product-receiving recesses that are each spanned by the film, and wherein the film has one pull-off strip per product-receiving recess to permit individual product removal.

5. The package of claim 1, wherein the product holder has an upwardly open groove which extends from the product-receiving recess to a lateral edge of the product holder and which is spanned by the pull-off strip.

6. The package of claim 1, wherein the product holder has an auxiliary product-receiving recess which is spanned by the film and has an opening tab to permit removal of the auxiliary product, the opening tab being defined by a further weakening of the film.

7. The package of claim 6, wherein the product holder has several auxiliary product-receiving recesses that are each spanned by the film, and wherein the film has one opening tab per auxiliary product-receiving recess, to permit individual opening of each auxiliary product-receiving recess.

8. The package of claim 6, wherein a laterally and upwardly open auxiliary recess is provided between the auxiliary product-receiving recess and a side face of the product holder.

9. The package of claim 1, wherein the product holder is arranged in a shell of a box with a removable lid.

* * * * *